(12) United States Patent
Rathjen

(10) Patent No.: US 8,727,532 B2
(45) Date of Patent: May 20, 2014

(54) OPHTHALMOLOGICAL MEASUREMENT APPARATUS AND MEASUREMENT METHOD

(75) Inventor: Christian Rathjen, Bremen (DE)

(73) Assignee: SIS AG, Surgical Instrument Systems (CH)

( * ) Notice: Subject to any disclaimer, the term of this patent is extended or adjusted under 35 U.S.C. 154(b) by 0 days.

(21) Appl. No.: 12/179,163

(22) Filed: Jul. 24, 2008

(65) Prior Publication Data

US 2010/0014051 A1 Jan. 21, 2010

Related U.S. Application Data

(60) Provisional application No. 60/935,062, filed on Jul. 24, 2007.

(51) Int. Cl.
*A61B 3/10* (2006.01)
*A61B 3/14* (2006.01)

(52) U.S. Cl.
CPC .... *A61B 3/10* (2013.01); *A61B 3/14* (2013.01)
USPC .......................................... 351/206; 351/246

(58) Field of Classification Search
CPC ............ A61B 3/10; A61B 3/14; A61B 3/113; A61B 3/107; A61B 3/1015; A61B 3/1005; A61B 3/0025
USPC .................................. 351/200, 205, 206, 246
See application file for complete search history.

(56) References Cited

U.S. PATENT DOCUMENTS

| | | | |
|---|---|---|---|
| 5,347,328 A | 9/1994 | Sekine et al. | |
| 5,387,951 A * | 2/1995 | Hatanaka | 351/205 |
| 5,847,827 A * | 12/1998 | Fercher | 356/493 |
| 6,454,761 B1 | 9/2002 | Freedman | |
| 6,779,891 B1 | 8/2004 | Barth et al. | |
| 2005/0203422 A1 | 9/2005 | Wei | |

FOREIGN PATENT DOCUMENTS

| | | |
|---|---|---|
| DE | 197 13 138 | 10/1998 |
| EP | 1430829 | 6/2004 |
| WO | WO 02/17775 | 3/2002 |
| WO | WO 2005/074789 | 8/2005 |

OTHER PUBLICATIONS

M. Wojtkowski, et al. "*In Vivo Human Retinal Imaging by Fourier Domain Optical Coherence Tomography*", Journal of Biomedical Optics, SPIE, Bellingham, WA, US, Bd. 7, Nr. 3, Jul. 2002.

* cited by examiner

*Primary Examiner* — James Greece
(74) *Attorney, Agent, or Firm* — Ostrolenk Faber LLP

(57) ABSTRACT

An ophthalmological measurement apparatus (10) for determining the axial length ($L_A$) of an eye (4) includes an optical interferometric first measurement system (1) for determining a relative position (A) of the retina (41) of the eye (4), a non-interferometric second measurement system (2) for determining a relative position (B) of the cornea (42) of the eye (4), and processing means (3) for determining the axial length ($L_A$) of the eye (4) on the basis of the relative position (A) of the retina (41) and of the relative position (B) of the cornea (42). The design of the ophthalmological measurement apparatus (10) with an interferometric and a non-interferometric measurement system for a different measuring range in each case on a measurement axis (z) enables the substantially simultaneous determination of the relative positions (A, B) both of the cornea (42) and of the retina (41) without this requiring differently dimensioned optical acquisition systems for determining interference patterns of light reflected at the retina (41) and at the cornea (42).

24 Claims, 11 Drawing Sheets

OPHTHALMOLOGICAL MEASUREMENT APPARATUS AND MEASUREMENT METHOD

CROSS-REFERENCE TO RELATED APPLICATIONS

The present application claims the benefit and priority of U.S. Provisional Application No. 60/935,062 filed Jul. 24, 2007 and entitled OPHTHALMOLOGICAL MEASUREMENT APPARATUS AND MEASUREMENT METHOD, the entire contents of which are hereby incorporated by reference herein.

BACKGROUND

1. Field of the Disclosure

The present application relates to an ophthalmological measurement apparatus and an ophthalmological measurement method for determining the axial length of an eye. The present application relates, in particular, to an ophthalmological measurement apparatus and an ophthalmological measurement method for contactlessly determining the axial length of the eye.

2. Related Art

As is explained, for example, in U.S. Pat. No. 5,347,328, conventional apparatuses for the interferometric measurement of the axial eye length, in which laser beams having a parallel beam profile converging on the retina are radiated onto the eye, have the disadvantage that the light reflected by the retina can be received outside the eye with a parallel beam path, whereas the light reflected by the cornea is reflected divergently through the cornea such that different wavefront profiles result for the light reflected by the retina and the light reflected by the cornea. During the detection of interference patterns with the aid of light receivers of small area, the different wavefront profiles result in only weak signals which can scarcely be distinguished from the noise caused by the rough retina surface, and during the detection with the aid of light receivers of large area a number of interference patterns result which reduce the signal modulation and therefore also do not permit unique conclusions relating to the distance between cornea and retina. In order to overcome these problems, in accordance with U.S. Pat. No. 5,347,328 the light reflected by the cornea and the light reflected by the retina is fed to different optical light acquisition systems by means of a beam splitter. The light received in the different light acquisition systems is combined, and interference is determined, in an optical interference light receiver. In accordance with U.S. Pat. No. 5,347,328, it follows that two differently dimensioned optical illumination and acquisition systems are required for acquiring the light reflected at the cornea and the light reflected at the retina, and for the interferometric determination, based thereon, of the axial eye length. Furthermore, avoiding parasitic inference requires the use of a path length compensation which sets the acquisition systems to exactly the same optical path lengths. It can be said in general that the simultaneous acquisition of retina and cornea requires twice as high an outlay on hardware by comparison with the simple Michelson interferometer. Avoiding measuring errors owing to axial eye movements during the measurement procedure requires simultaneous acquisition. U.S. Pat. No. 5,347,328, as well as U.S. Pat. No. 6,779,891 make use for this purpose of interferometric designs which can determine only the relative spacing of optical interfaces, but not the distance from the measuring instrument. When there are more than two optical interfaces, their position relative to one another cannot be determined uniquely. Were such measurement methods to be used to determine further intraocular distances, it would, for example, be impossible to distinguish between the anterior chamber depth and the lens thickness.

SUMMARY

It is an object of the present disclosure to propose an ophthalmological measurement apparatus and an ophthalmological measurement method for determining the axial length of an eye, which do not have at least certain disadvantages of the prior art; in particular, the aim is not to require differently dimensioned optical acquisition systems for determining interference patterns of light reflected at the retina and at the cornea.

It is an object of the present disclosure to propose an ophthalmological measurement apparatus and an ophthalmological measurement method for determining the axial length of an eye, which do not have at least certain disadvantages of the prior art; in particular, the aim is not to require differently dimensioned optical acquisition systems for determining interference patterns of light reflected at the retina and at the cornea.

In accordance with the present disclosure, these aims are achieved, in particular, by the elements of the independent claims. Further advantageous embodiments emerge, moreover, from the dependent claims and the description.

The above named aims are achieved by the present disclosure owing to the fact, in particular, that the ophthalmological measurement apparatus for determining the axial length of an eye comprises an optical interferometric first measurement system for determining a relative position of the retina of the eye, that the ophthalmological measurement apparatus additionally comprises a non-interferometric second measurement system for determining a relative position of the cornea of the eye, and that the ophthalmological measurement apparatus comprises processing means for determining the axial length of the eye on the basis of the relative position, determined by the interferometric measurement system, of the retina and of the relative position, determined by the non-interferometric measurement system, of the cornea. The interferometric measurement system preferably comprises an apparatus for optical coherence tomography with depth scanning. What is meant by the term "relative position" is a defined geometrical position, for example with reference to the ophthalmological apparatus and, for example, to a defined measurement axis. The design of the ophthalmological measurement apparatus with an interferometric and a non-interferometric measurement system for a different measuring range in each case on a measurement axis, in particular for a first measuring range in the cornea region and a second measuring range in the retina region, enables the substantially simultaneous determination of the relative positions both of the cornea and of the retina without this requiring differently dimensioned optical acquisition systems for determining interference patterns of light reflected at the retina and at the cornea. This gives rise, firstly, to the advantage that the interferometric system can be entirely optimized in relation to the signal quality of the retinal measurement. Secondly, there are no disturbances which could be caused by another interferometric system. By comparison with the prior art, this enables determination of the axial eye length which is substantially easier in terms of hardware and is not impaired by eye movements on the basis of the simultaneous acquisition of retina and cornea. The combination of interferometric and non-interferometric measurement additionally enables not only the unique determination of the axial eye length, but, moreover, in conjunction with the non-interferometrically determined relative corneal position as unique reference point in corresponding design variants, also enables the determination of the anterior chamber depth (from the outer corneal surface up to the lens of the eye) and the lens thickness. Moreover, there are further advantages owing to the determination of a relative position in relation to the measuring instrument. For example, this information can be used without additional aids in order to facilitate the positioning of the patient. Furthermore, the combination of interferometric and non-interferometric measurement systems results in cost advantages by comparison with the configuration of known systems, which is more complex in terms of hardware, said systems simultaneously acquiring the retina and cornea by means of interferometric metrology.

Moreover, in order to determine the anterior chamber depth, the interferometric measurement system or the non-interferometric measurement system is set up to determine the relative position of the front side, facing the cornea, of the lens of the eye, and the processing means are additionally set up to determine the anterior chamber depth of the eye on the basis of the relative position of the cornea and of the relative position of the facing front side of the lens. Moreover, in order to determine the lens thickness, the interferometric measurement system or the non-interferometric measurement system is set up to determine the relative position of the front side, facing the cornea, of the lens, and the interferometric measurement system is additionally set up to determine the relative position of the rear side, averted from the cornea, of the lens, and the processing means are additionally set up to determine the thickness of the lens on the basis of the relative positions of the facing front side and the relative positions of the averted rear side.

In one design variant, the non-interferometric measurement system comprises a light barrier system for detecting the vertex of the cornea as relative position of the cornea. The light barrier system is coupled to the first measurement system such that the detection of the vertex automatically activates the interferometric measurement system in order to determine the relative position of the retina. Particularly in the case of the use of optical coherence tomography (OCT), without moving optical parts for depth scanning (this also being denoted as static depth scanning), that is to say without a variable reference arm length, the resolution of the interferometric measurement of the retina by the light barrier detection of the cornea enables an only slightly delayed, substantially simultaneous determination of the relative positions of the cornea and retina, and thus determination of the axial eye length is not impaired by eye movements.

In various alternative design variants, the non-interferometric measurement system comprises a distance measurement system for determining the relative position of the cornea on the basis of light diffusely reflected and/or scattered by the eye, or on the basis of light specularly reflected by the cornea.

The non-interferometric measurement system preferably comprises a light projector for projecting at least one light beam onto the cornea, and a light receiver connected to the processing means. The processing means are additionally set up to determine the relative position of the cornea on the basis of a signal received and acquired by the light receiver. In different design variants, the light projector and the light receiver are combined and arranged such that the relative position of the cornea is determined by light barrier detection, or by distance measurement on the basis of diffuse reflection/scattering or specular reflection.

In one design variant, the light projector is set up to project two light beams intersecting at a crossing point, and the light receiver is set up to detect the positioning of the crossing point on the cornea in order to determine the relative position of the cornea. In addition to the use for distance measurement, the detection of the crossing point on the cornea can also be used for the light barrier detection of the cornea.

In a further design variant, the non-interferometric measurement system comprises an optical system, for example a lens, for focussed projection of the light beam onto the cornea, and a pinhole diaphragm placed upstream of the light receiver. In this case, the optical system and the pinhole diaphragm are arranged such that the light beam reflected by the cornea is fed to the light receiver via the optical system and through the pinhole diaphragm in order to determine the relative position of the cornea. By way of example, in the case of a positioning of an optical lens in the middle between cornea and pinhole diaphragm, the light beam reflected by the cornea is fed in a focussed fashion through the pinhole diaphragm to the light receiver in order to determine the relative position of the cornea. In addition to the use for distance measurement, the detection of a defined position of the cornea relative to the pinhole diaphragm can also be used for the light barrier detection of the cornea.

In one design variant, the distance measurement system comprises an autofocus sensor for determining the relative position of the cornea. The autofocus sensor is based, for example, on a light barrier detection with automatic displacement of the entire light barrier, the pinhole diaphragm described above, or the light projectors for the intersecting light beams.

In a further design variant, the distance measurement system comprises a sensor for detecting wavelength-dependent focal points when focussing a broadband light source with the aid of an optical system having strong chromatic aberrations, and the processing means are set up to determine the relative position of the cornea on the basis of the chromatic aberration.

In another design variant, the light projector is set up to project the light beam along a measurement axis through a cross-sectional part of the cornea, and the light receiver is set up to acquire and store a cross-sectional image of the cross-sectional part, illuminated by the light projector, in the Scheimpflug arrangement with respect to the light beam. The processing means are set up to determine the relative position of the cornea on the measurement axis on the basis of the cross-sectional image and the relative position of the retina determined by the interferometric measurement system on the measurement axis.

In a further design variant, the first measurement system is coupled, directly or via a control module, to the second measurement system such that a signal from the first measurement system indicating the detection of the relative position of the retina automatically activates the second measurement system to determine the relative position of the cornea. Particularly in the case of the use of optical coherence tomography with a reference arm length which can be varied in order to determine the relative position of the retina (also denoted as dynamic depth scanning), the resolution of the non-interferometric measurement of the cornea permits, by means of the interferometric determination of the relative position of the retina, only a slightly delayed, substantially simultaneous determination of the relative positions of cornea and retina, and thus the determination of the axial eye length which is not impaired by eye movements. It is also possible to displace the entire interferometer in addition to varying the reference arm length.

In an alternative design variant, the interferometric measurement system and the non-interferometric measurement system are connected to the processing means and set up to transmit continuously to the processing means signals for determining the current relative position of the retina and for determining the current relative position of the cornea. The processing means are set up appropriately to determine a currently ascertained value of the axial length of the eye on the basis of the current relative position of the retina and the current relative position of the cornea.

In a further design variant, the interferometric measurement system and the non-interferometric measurement system each comprise a light source for generating a light beam, the wavelengths of the light beams generated by the light sources being different from one another. The generation and use of light beams with different wavelengths permits the substantially simultaneous determination of the relative positions of retina and cornea without mutual influence and disturbance of the interferometric and non-interferometric measurement systems. It may be added at this juncture that, in an alternative design variant for the two measurement systems, a common light source or two light sources of identical wavelength are used, the non-interferometric system being designed such that it is not disturbed by the interferometric measurement system (for example via field stops or confocal images).

Alongside the ophthalmological measurement apparatus for determining the axial length of an eye, the present invention additionally relates to a measurement method for contactlessly determining the axial length of an eye, in which a relative position of the retina of the eye is determined by means of an optical interferometric measurement system, in which a relative position of the cornea of the eye is determined by means of a non-interferometric measurement system, and in which the axial length of the eye is calculated on the basis of the interferometrically determined relative position of the retina and the non-interferometrically determined relative position of the cornea. In different design variants, a vertex of the cornea is detected as relative position of the cornea by means of a light barrier system, and upon detection of the vertex the optical interferometric measurement system is automatically activated in order to determine the relative position of the retina, or the relative position of the retina is determined by means of an apparatus for optical coherence tomography, for example by varying a reference arm length, and upon detection of a signal indicating the relative position of the retina the relative position of the cornea is automatically determined by means of the non-interferometric measurement system, for example at the current reference arm length (for example the current position of the reference arm mirror). In addition, there is also the possibility of continuously determining current relative positions of the retina and the cornea by means of the interferometric measurement system and the non-interferometric measurement system, and of calculating a current value of the axial length of the eye on the basis thereof. In order to calibrate the ophthalmological measurement apparatus, before the determination of the relative position of the retina and of the relative position of the cornea, a first relative position of a reference body is determined by means of the non-interferometric measurement system, a second relative position of the reference body is determined by means of the optical interferometric measurement system, and deviations between the first relative position of the reference body and the second relative position of the reference body are acquired and taken into account when determining the axial length of the eye.

BRIEF DESCRIPTION OF THE DRAWINGS

A design of the present disclosure is described below with the aid of an example. The example of the design is illustrated by the following attached figures.

DETAILED DESCRIPTION OF THE EMBODIMENTS

In FIGS. 1 to 11, identical reference symbols denote components and systems corresponding to one another functionally; the specific designs of these components corresponding to one another functionally can, however, vary in different design variants.

Figure 1:
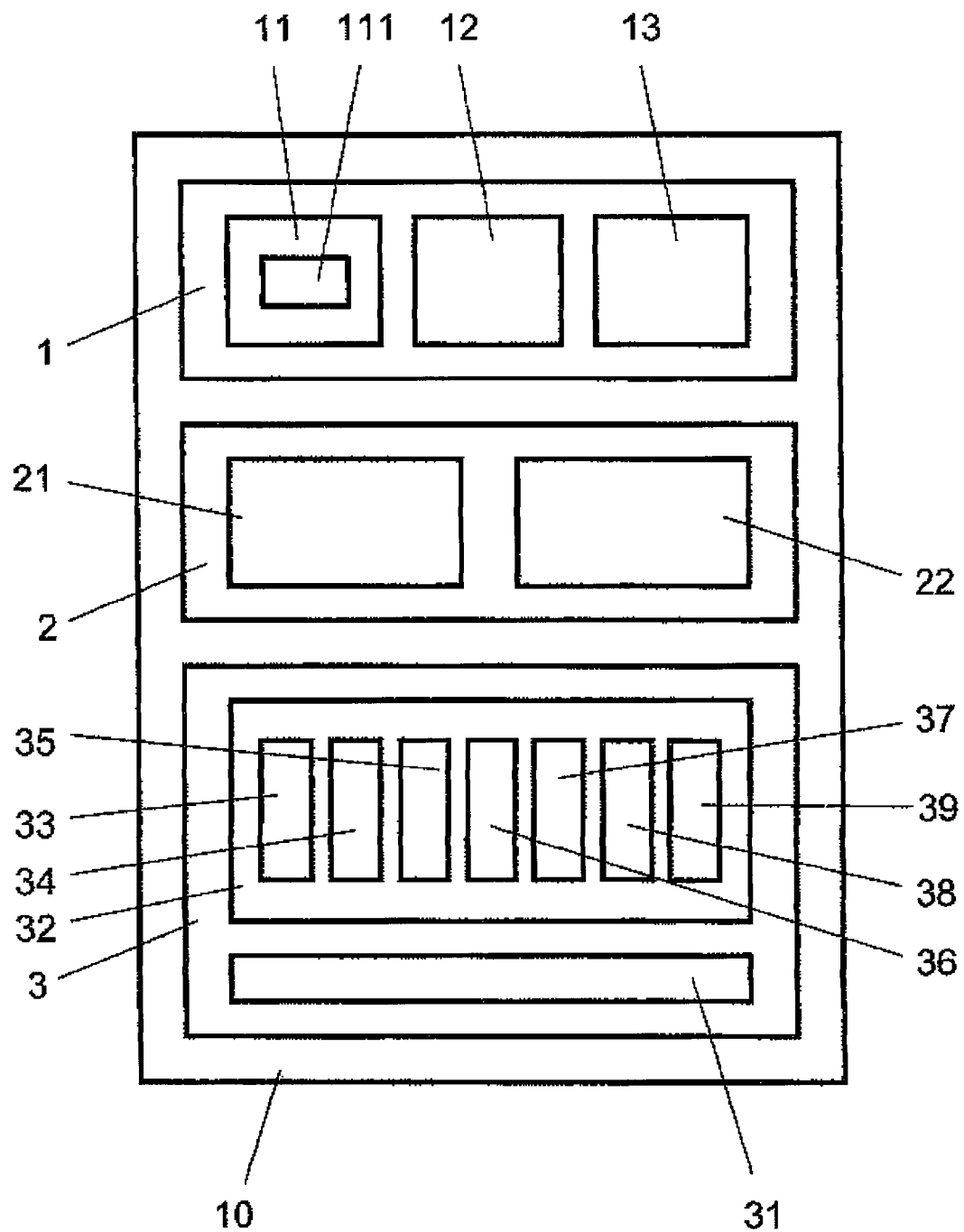
FIG. 1 shows a block diagram which schematically illustrates an ophthalmological measurement apparatus which comprises an interferometric measurement system, a non-interferometric measurement system and processing means.
Figure 2:
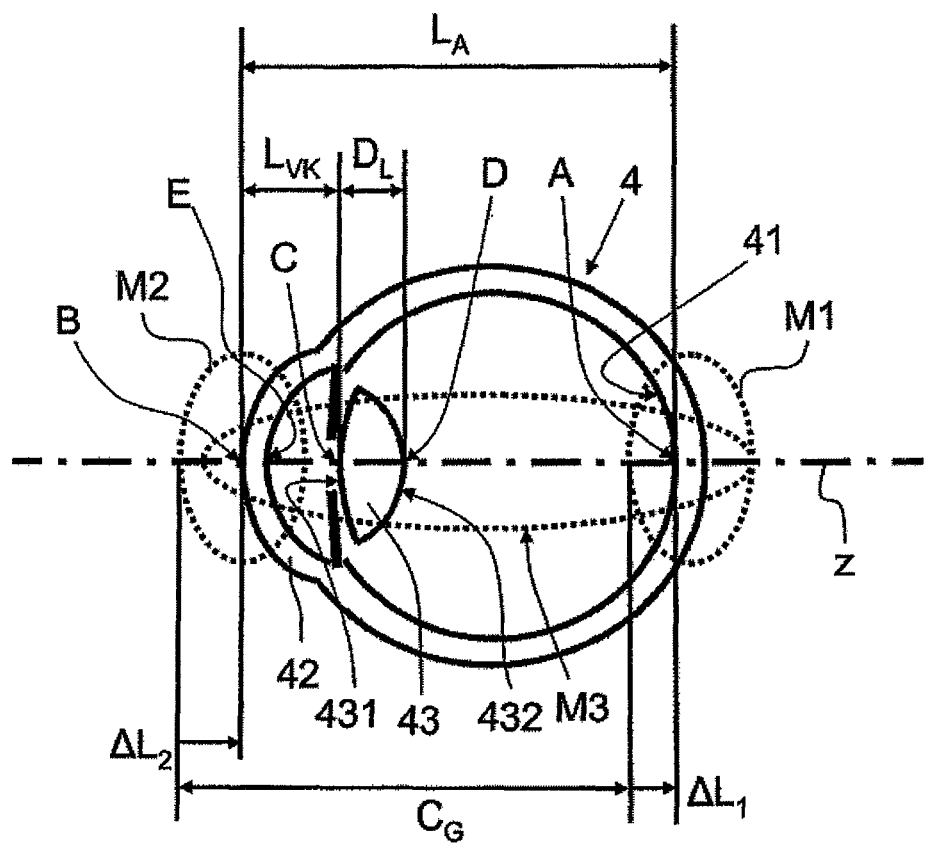
FIG. 2 shows a diagrammatic cross-sectional image of an eye with a first measurement region in the area of the cornea, and a second measurement region in the area of the retina.

FIG. 1 illustrates an ophthalmological measurement apparatus 10 for determining the axial length $L_A$ of an eye 4 illustrated in FIG. 2. The ophthalmological measurement apparatus 10 comprises an interferometric measurement system 1 for determining a relative position A of the retina 41 on the measurement axis z. As illustrated diagrammatically in FIG. 1, the interferometric measurement system 1 comprises a coherent or partially coherent light source 111, beam-splitting and beam-combining means 12 (for example a beam-splitting prism), a light projector 11, a reference arm 14 with mirror, and a light detector 13. The ophthalmological measurement apparatus 10 additionally comprises a non-interferometric measurement system 2 for determining a relative position B of the cornea 42 on the measurement axis z. The measurement axis z preferably corresponds to a longitudinal axis of the eye 4, for example the optical axis or the visual axis. The relative position B of the cornea 42 on the measurement axis z corresponds to the vertex of the cornea 42. As is illustrated diagrammatically in FIG. 1, the non-interferometric measurement system 2 comprises a light projector 21 and a light receiver 22. The ophthalmological measurement apparatus 10 moreover comprises processing means 3 having a processor 21 and a program and data memory 32 in which various programmed software modules for controlling the processor 31 are stored. The software modules comprise, for example, a calculation module 33, an FFT module 34, a triangulation module 35, a spectroscopy module 36, a detection module 37, a control module 38 and/or an image processing module 39. The interferometric measurement system 1 is preferably set up to determine the relative position A of the retina 41 within a first measuring range M1 on the measurement axis z. The non-interferometric measurement system 2 is preferably set up to determine the relative position B of the cornea 42 within a second measuring range M2 on the measurement axis z. In a preferred design variant, the interferometric measurement system 1 is set up for calibration purposes and for determining (on the measurement axis z) the relative position E of the rear side of the cornea 42, the relative position C of the front side 431, facing the cornea 42, of the lens 43, and to cover the extended measuring range M3 in order to determine the relative position D of the rear side 432, averted from cornea 42, of the lens 43 (for example via a variation in the reference arm length). A variation in the reference arm length can be used to extend the measuring range of fast interferometric methods having a limited measuring range. The processing means 3 comprise a calculation module 33 which is set up to calculate the axial length $L_A$ of the eye 4 from the relative position A of the retina 41 and the relative position B of the cornea 42. The calculation module 33 is additionally set up to calculate the anterior chamber depth $L_{VK}$ from the relative position B of the cornea 42 and the relative position C of the front side 431 of the lens 43, to calculate the thickness $D_L$ of the lens 43 from the relative position C of the front side 431 of the lens 43 and the relative position D of the rear side 432 of the lens 43, and/or to calculate the thickness of the cornea 42 from the relative positions B and E of the front and rear sides, respectively, of the cornea 42. The calculation module 33 is additionally set up to indicate the calculated values of the axial length $L_A$, of the anterior chamber depth $L_{VK}$, of the corneal thickness and/or the thickness $D_L$ of the lens on a display of the ophthalmological measurement apparatus 10.

Figure 3:
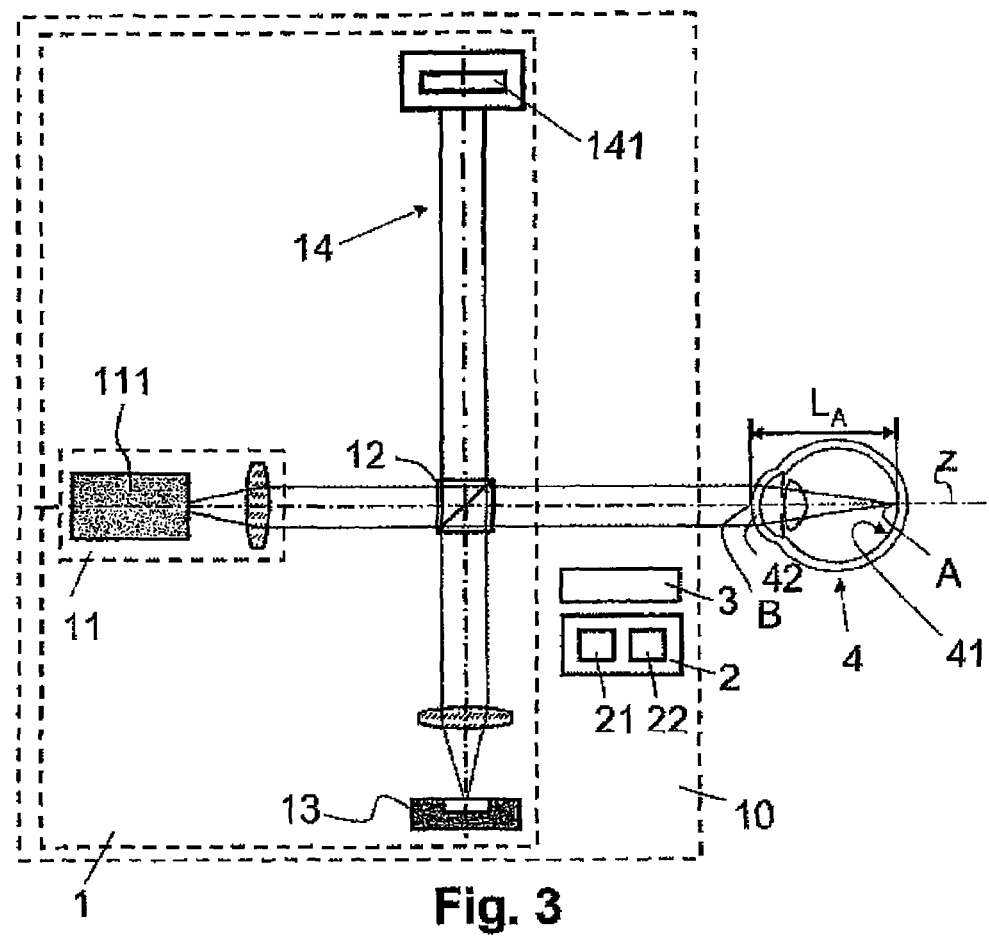
FIG. 3 shows a block diagram which schematically illustrates an ophthalmological measurement apparatus in which the interferometric measurement system comprises an apparatus for optical coherence tomography with depth scanning.
Figure 5:
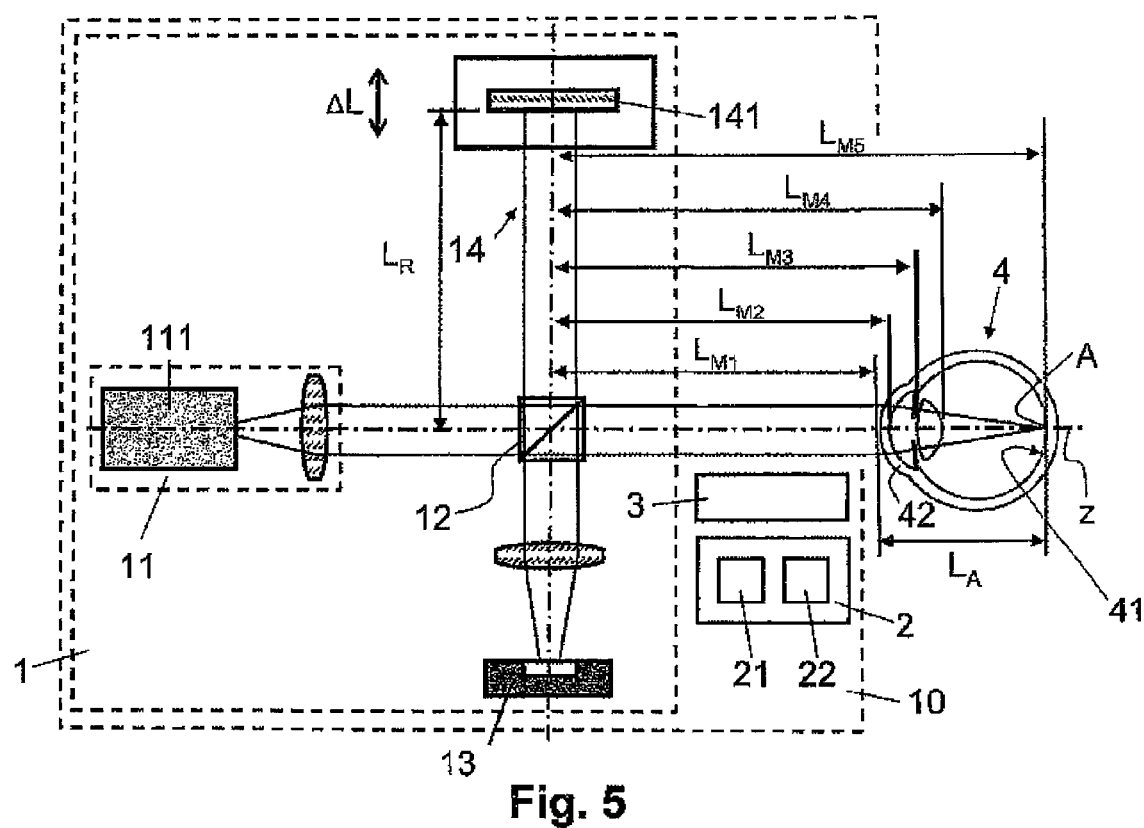
FIG. 5 shows a block diagram which schematically illustrates an ophthalmological measurement apparatus in which the interferometric measurement system is designed as a Michelson interferometer with variable reference arm length.
Figure 11:
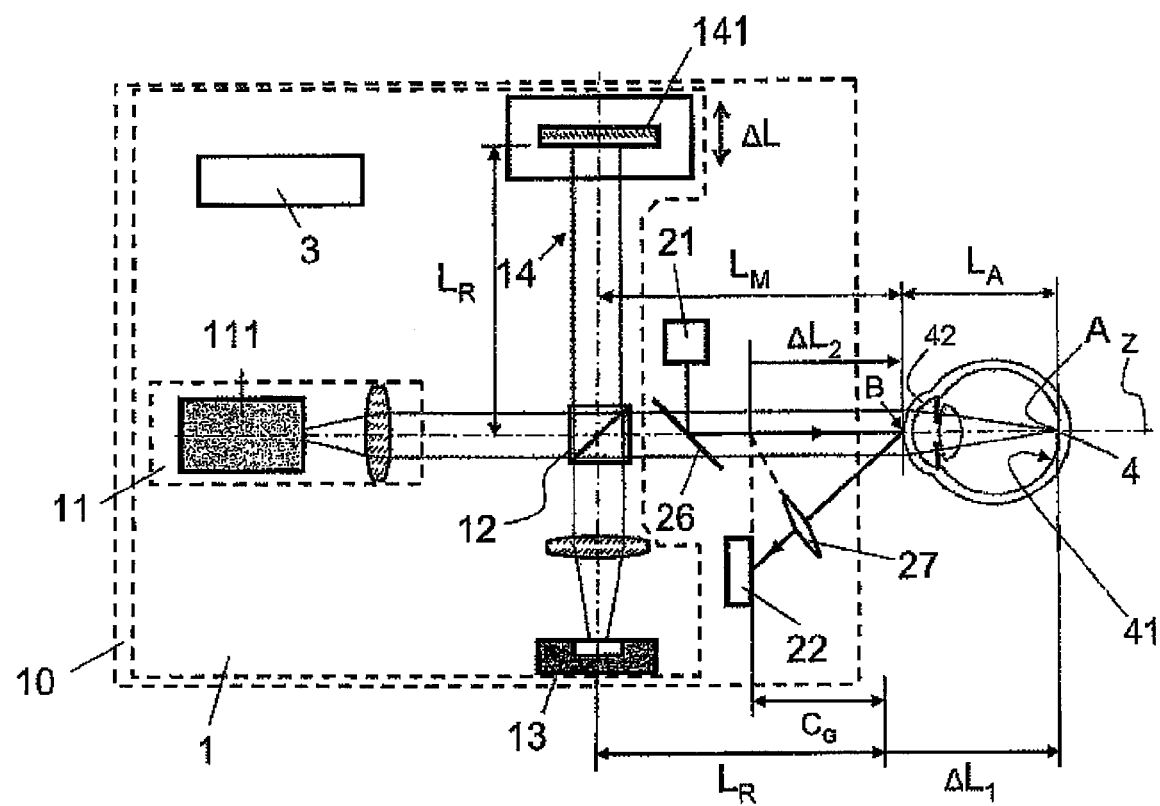
FIG. 11 shows a block diagram which schematically illustrates an ophthalmological measurement apparatus in which the interferometric measurement system is designed as a Michelson interferometer with variable reference arm lengths and the non-interferometric measurement system is designed with a light receiver and light projector in the Scheimpflug arrangement for determining the cornea by triangulation.

FIGS. 3, 5 and 11 illustrate the ophthalmological measurement apparatus 10 with in each case an interferometric measurement system 1 which is set up for optical coherence tomography (OCT) with depth scanning. The interferometric measurement system 1, or the apparatus for optical coherence tomography with depth scanning, comprises a light projector 11 having a light source 111, a beam splitter 12, a reference arm 14, and a light detector 13. The interferometric measurement system 1 in accordance with the variant according to FIG. 3 is set up for static depth scanning (without variable reference arm length). In a design variant, the interferometric measurement system 1 according to FIG. 3 is designed as a so-called swept source OCT (SSOCT), and comprises a light source 111 of variable wavelength and a detector 13 with a simple yet highly sensitive photodiode. The interferometric measurement system 1 according to FIG. 3 can also be designed as a frequency domain OCT (FDOCT) or Fourier (transform) OCT (FOCT) with a broadband light source 111 and a suitable detector 13 (for example diffraction grating with CCD row). In the design variant according to FIGS. 5 and 11, the interferometric measurement system 1 is designed as a so-called Michelson interferometer or Time Domain OCT (TOCT) with a variable reference arm length (displaceable mirror 141 in the reference arm 14), broadband light source 111 and detector 13 with a simple but highly sensitive diode. The variation in the reference arm length as well as different suitable methods for signal processing are described in EP0581871, for example.

Figure 4:
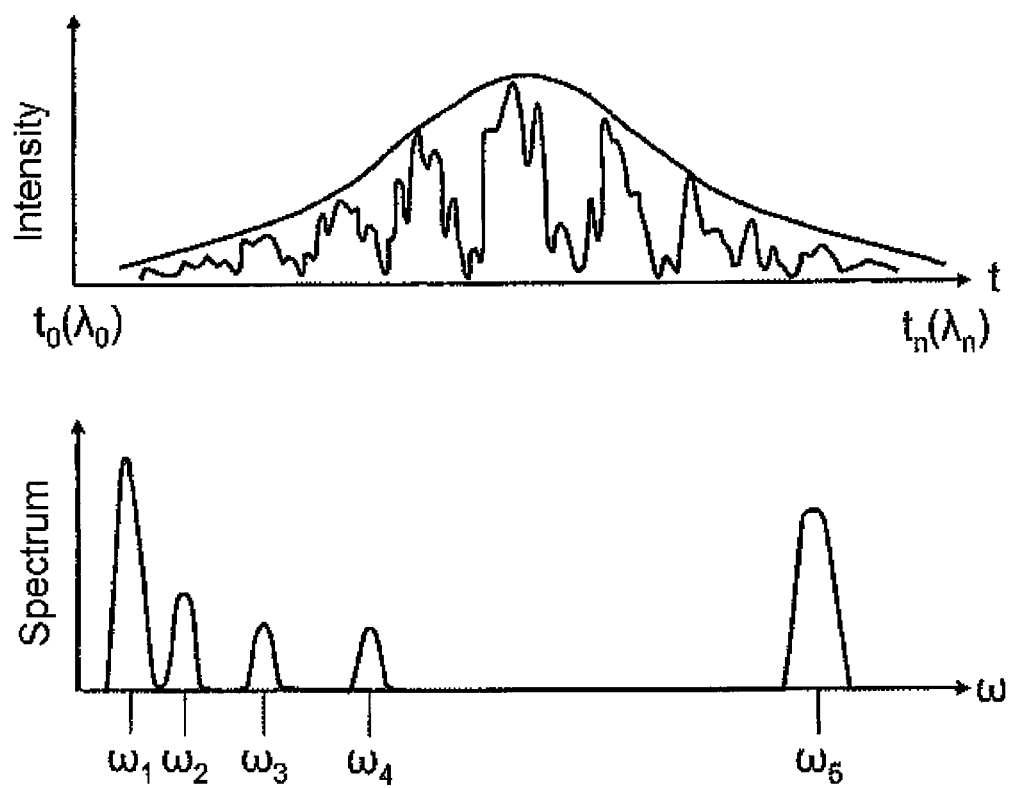
FIG. 4 shows a graph of an intensity signal in the time domain (top), and of a spectrum in the frequency domain (bottom) which result from the static interferometric depth scanning of an eye.

FIG. 4 illustrates the intensity signal, detected by the detector 13, in the time domain (top), and the spectrum in the frequency domain (bottom) in the case of a depth scanning of the eye 4 by means of the interferometric measurement system 1, illustrated in FIG. 3, in the SSOCT design. The intensity signal is illustrated for the wavelength $\lambda_0$ at the instant $t_0$ up to the wavelength $\lambda_n$ at the instant $t_n$. The processing means comprise an optical FFT module 34 (Fast Fourier Transformation) for determining the frequency spectrum. The interference-forming boundary layers in the eye 4 are visible in the frequency spectrum, and in this case the modulation frequencies $\omega_1, \omega_2, \omega_3, \omega_4, \omega_5$ correspond to the relative positions (or lengths) of the boundary layers and can be used to determine the relative position A of the retina 41 ($\omega_5$), the relative position C of the front side 431 ($\omega_3$) of the lens 43 and the relative position D of the rear side 432 ($\omega_4$) of the lens 43. In particular, via the base position $\omega_1$ the frequency spectrum enables the relative positioning and/or calibration of the relative positions determined by the interferometric measurement system 1 in relation to the relative position B, determined by the non-interferometric measurement system 2, of the cornea or in relation to the geometry of the ophthalmological measurement apparatus 10 (for example by means of a reference body which can be acquired by the two measurement systems).

Figure 6:
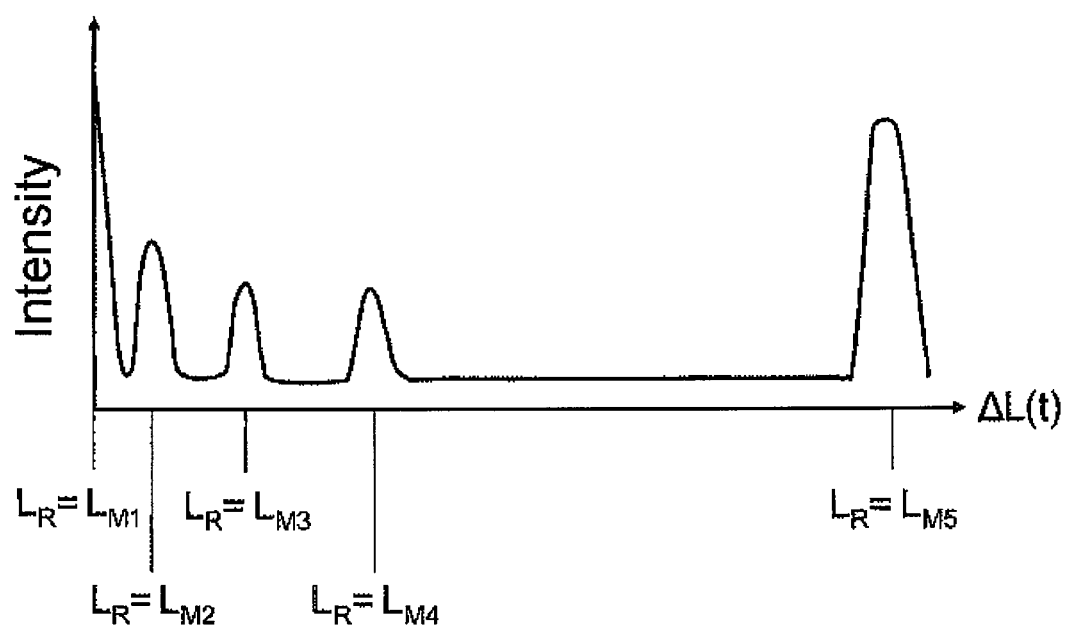
FIG. 6 shows a graph of an intensity signal in the time domain which results from the interferometric depth scanning of the eye by means of a variable reference arm length.

FIG. 6 illustrates the intensity signal, detected by the detector 13, in the time domain in the case of a depth scanning of the eye 4 by means of a variable reference arm length (for example via a displaceable mirror 141) of the interferometric measurement system 1, illustrated in FIGS. 5 and 11, in the TOCT design. The intensity signal is illustrated as a function of the displacement ΔL (scanning distance) of the reference arm 14. The interference-forming boundary layers in the eye 4 are visible in the time domain as a function of the displacement, in which case the measurement arm lengths $L_{M1}, L_{M2}, L_{M3}, L_{M4}$ and $L_{M5}$ correspond to the relative positions (or lengths) of the boundary layers and can be used to determine the relative position A of the retina 41 ($L_{M5}$), the relative position C of the front side 431 ($L_{M3}$) of the lens 43 and the relative position D of the rear side 432 ($L_{M4}$) of the lens 43. In particular, via the base position $L_{M1}$ the intensity signal permits the relative positioning and/or calibration of the relative positions, determined by the interferometric measurement system 1, relative to the relative position B, determined by the non-interferometric measurement system 2, of the cornea or relative to the geometry of the ophthalmological measurement apparatus 10.

In a preferred design variant, the interferometric measurement system 1 according to one of FIGS. 3, 5 and 11 is coupled directly or via an optional control module 38 to the non-interferometric measurement system 2 according to one of FIGS. 7, 8, 9, 10a, 10b, 10c or 11, such that a signal which indicates the interferometric detection of the retina 41 automatically activates the non-interferometric determination of the relative position B of the cornea 42 by the non-interferometric measurement system 2. The signal indicating the interferometric detection of the retina 41 is, for example, determined automatically by an optional detection module 37 of the processing means on the basis of the spectrum profile in accordance with FIG. 4 (bottom) or of the intensity signal according to FIG. 6. The calculation module 33 automatically calculates the axial length $L_A$ of the eye 4 from the relative position A of the retina 41 and the relative position B of the cornea 42 as soon as the determination, triggered by the interferometric measurement system 1, of the relative position B of the cornea 42 by the non-interferometric measurement system 2 is present. In an alternative design, the calculation module 33 calculates the axial length $L_A$ of the eye 4 continuously from current values of the relative position A of the retina 41 and the relative position B of the cornea 42.

FIGS. 7, 8, 9, 10a, 10b and 10c illustrate various embodiments for the non-interferometric measurement system 2 which in each case can be combined as different design variants with a variant of the interferometric measurement system 1, in particular with the embodiments, illustrated in FIGS. 3 and 5, of the interferometric measurement system 1. Moreover, it may be remarked that the invention relates not only to Michelson interferometers, but can in principle be implemented with the aid of all the interferometers which supply a relative position with reference to the measuring instrument.

Figure 7:
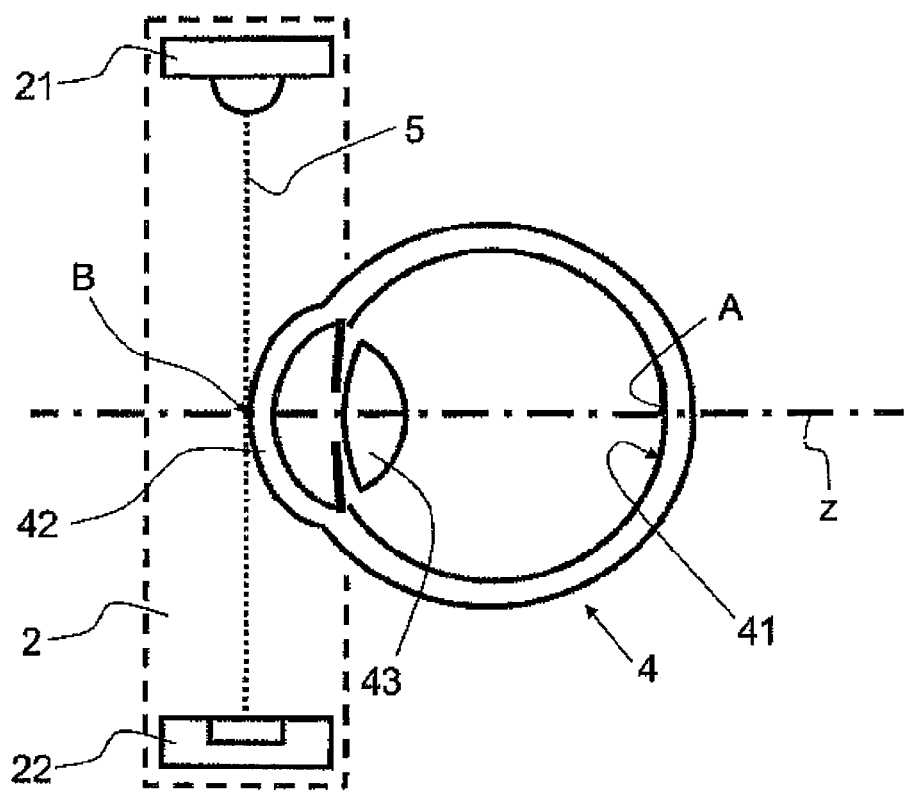
FIG. 7 shows a block diagram which schematically illustrates an ophthalmological measurement apparatus in which the non-interferometric measurement system is designed as a light barrier.

In the design variant according to FIG. 7, the light projector 21 and the light receiver 22 of the non-interferometric measurement system 2 are arranged as a light barrier such that the vertex of the cornea 42 can be detected as relative position on the measurement axis z. That is to say, the ophthalmological measurement apparatus 10 can be positioned such that the non-interferometric measurement system 2 covers the measuring range M2 and can determine the exact position of the cornea 42 with reference to the measurement axis z by detecting the vertex by means of the light barrier formed by the light projector 21, for example a collimated laser diode, and the light receiver 22, for example a photosensor, when the light beam 5 is interrupted.

Figure 8:
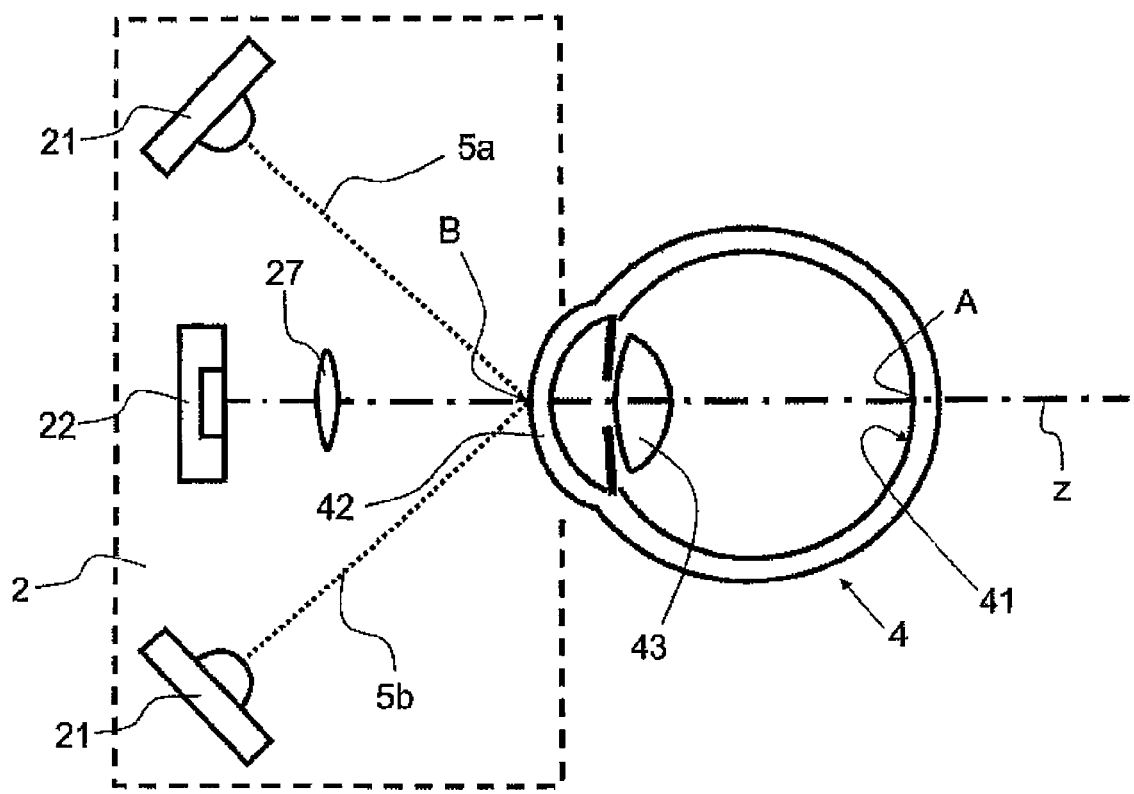
FIG. 8 shows a block diagram which schematically illustrates an ophthalmological measurement apparatus in which the non-interferometric measurement system projects two light beams intersecting at a crossing point in order to detect the cornea.

In the design variant according to FIG. 8, the non-interferometric measurement system 2 is set up to project two light beams 5a, 5b intersecting at a crossing point, for example by means of two light projectors 21 with a common light source and appropriately arranged mirrors. The light projectors 21, for example laser diodes, and the light receiver 22, for example a CCD camera, are arranged such that a positioning of the crossing point on the cornea 42 by the light receiver 22 can be detected in order to determine the relative position of the cornea 42. That is to say, the measuring range M2 can be covered by positioning the non-interferometric measurement system 2 such that the light receiver 22 can detect when the crossing point of the two light beams 5a, 5b comes to lie at the cornea 42, in particular at the vertex of the cornea 42, and the position of the cornea 42 can be determined with reference to the measurement axis z.

Figure 9:
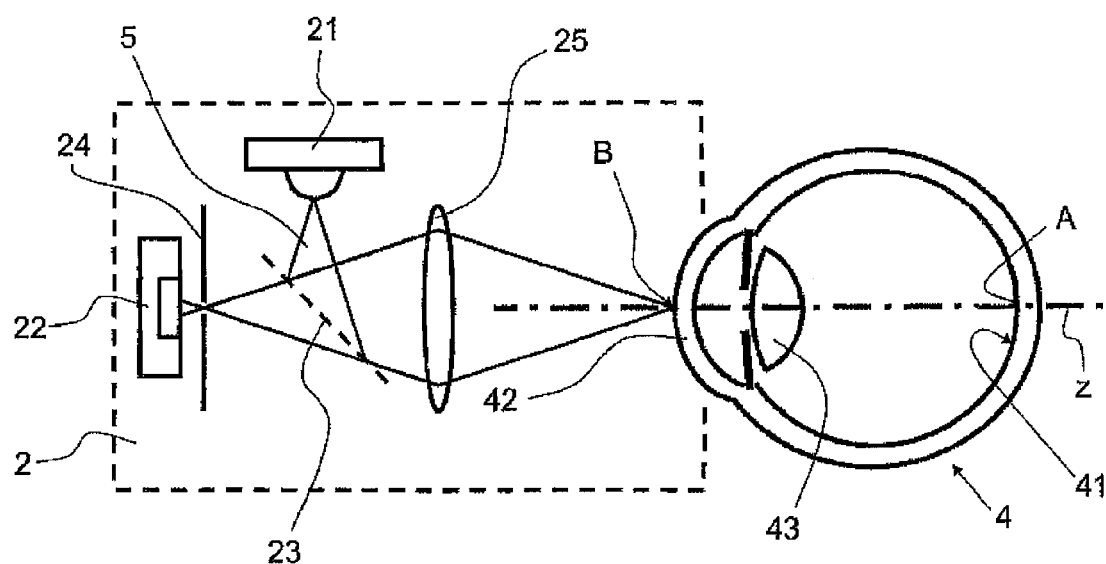
FIG. 9 shows a block diagram which schematically illustrates an ophthalmological measurement apparatus in which the non-interferometric measurement system comprises an optical lens and a pinhole diaphragm for confocally detecting the cornea.

In the design variant according to FIG. 9, in addition to the light projector 21 and to the light receiver 22, the non-interferometric measurement system 2 comprises a semitransparent mirror 23, a pinhole diaphragm 24 and an optical system 25, for example an optical lens. As is illustrated diagrammatically in FIG. 9, the light beam 5, for example a laser beam, output by the light projector 21 is projected in a focussed manner onto the cornea 42 via the mirror 23 and the optical system 25. The pinhole diaphragm 24 is, for example, arranged between the light receiver 22 and the optical lens 25 such that light reflected on the cornea 42 is fed to the light receiver, for example a photodiode, via the optical system 25 and the pinhole diaphragm 24 when the cornea 42, in particular the vertex of the cornea 42, has the same focal distance from the optical lens 25 as the pinhole diaphragm 24. That is to say, the measuring range M2 can be covered confocally by positioning the non-interferometric measurement system 2 such that the light receiver 22 can detect when the cornea 42, in particular the vertex of the cornea 42, comes to lie at the focus of the optical lens 25, and the position of the cornea 42 can be determined with reference to the measurement axis z. The optical system 25 and the pinhole diaphragm 24 are thus arranged such that, in order to determine the relative position B of the cornea 42, the light reflected by the cornea 42 is fed through the optical system 25 to the light receiver 22 when the focus of the reflected light comes to lie in the opening of the pinhole diaphragm 24.

In a further preferred design variant, the non-interferometric measurement system 2 according to one of FIG. 7, 8 or 9 is coupled, directly or via an optional control module 38, to the interferometric measurement system 1 such that a signal, which indicates the light barrier detection of the cornea 42 according to FIG. 7, the positioning of the crossing point on the cornea 42 according to FIG. 8, or the detection of the cornea 42 at the focal point according to FIG. 9, automatically activates the interferometric determination of, optionally, the relative position A of the retina, the relative position of the front side C of the lens 43, and/or the relative position of the rear side D of the lens 43 by means of the interferometric measurement system 1. The calculation module 33 automatically calculates the axial length $L_A$ of the eye 4 from the relative position A of the retina 41 and the relative position B of the cornea 42 as soon as the determination, triggered by the non-interferometric measurement system 2, of the relative position A of the retina 41 by the interferometric measurement system 1 is present. In an alternative design, the calculation module 33 calculates the axial length $L_A$ of the eye 4 continuously from current values of the relative position A of the retina 41 and the relative position B of the cornea 42.

In one variant, the non-interferometric measurement system 2 according to one of FIG. 7, 8 or 9 is designed as an autofocus system for automatically measuring the distance from the cornea 42, in particular from the vertex of the cornea 42. For this purpose, for example, the entire light barrier system according to FIG. 7, 8 or 9, the light projectors according to FIG. 8 or the pinhole diaphragm 24 according to FIG. 9 are automatically moved by a movement driver until the detection of the cornea 42. The movements can be converted into relative positions by suitable calibration.

In a further variant, the non-interferometric measurement system 2 comprises for distance measurement a light projector with strong chromatic aberrations, and a broadband light source, by means of which a wavelength-dependent focal position results. The processing means 3 comprise an optional spectroscopy module 36 which is set up to determine the relative position of the cornea 42, in particular of the vertex of the cornea 42, on the basis of the acquired spectra, for example via appropriate stored tables.

Figures 10A, 10B, 10C:
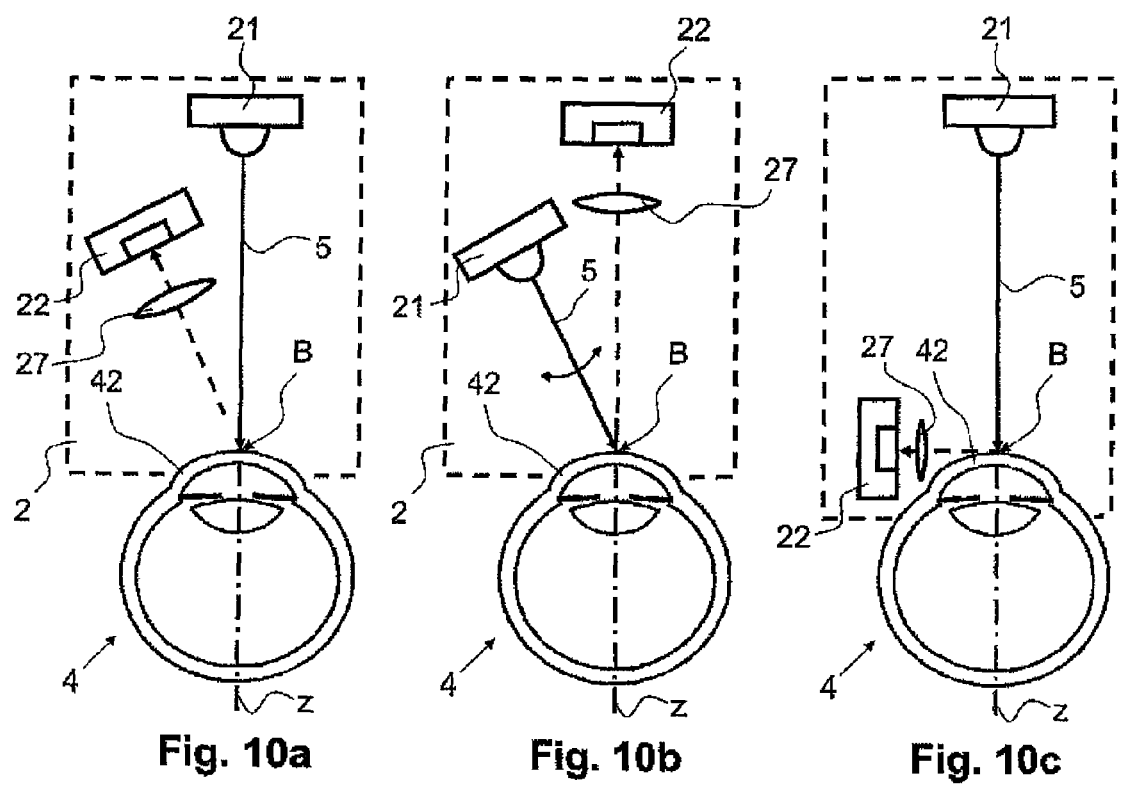
FIGS. 10a, 10b and 10c show block diagrams which each schematically illustrate a non-interferometric measurement system with differently arranged light projectors and light receivers for determining the cornea by triangulation.

Illustrated in FIGS. 10a, 10b and 10c are various arrangements of the light projector 21 and the light receiver 22 of the non-interferometric measurement system 2 which, by means of triangulation in each case, permit the determination of the relative position B of the cornea 42, in particular of the vertex of the cornea 42, on the basis of diffuse reflection on surfaces or scattering (in the case of transparency of the tissue to the wavelength use) in the eye tissue.

In the design variant according to FIG. 10a, a light beam 5 or (shaped) ray bundle, for example a laser beam, is radiated by the light projector 21 on to the eye 4 along the measurement axis z. The light receiver 22, for example a single-row CCD detector with an imaging optical system, is arranged outside the radiation axis and acquires from various positions the light which is reflected diffusely on surfaces of the eye 4 and, if appropriate, is scattered in the eye tissue. An optional triangulation module 35 is set up to determine the relative position B of the cornea 42, in particular of the vertex of the cornea 42, from the various acquired perspectives of the reflected and scattered light by means of triangulation methods. In a subvariant, the light receiver 22 is, for example, a CCD camera which is arranged in the Scheimpflug arrangement with respect to the light beam or ray bundle 5. FIG. 10c shows an arrangement in which the optical axis of the light receiver 22 is arranged perpendicular to the projection axis.

In the design variant according to FIG. 11, the ophthalmological measurement apparatus 10 comprises a combination of Michelson interferometer and non-interferometric measurement system 2 in the Scheimpflug arrangement. The interferometric measurement system 1 is designed as a TOCT system with a variable reference arm length (reference arm 14 with displaceable mirror 141), broadband light source 111 and detector 13 with a simple but highly sensitive photodiode. In the non-interferometric measurement system 2, the light beam of the light projector 21 is guided onto the measurement axis z via a semitransparent mirror 26, and the light diffusely reflected or scattered by the cornea 42 is directed via the optical lens 27 onto the light receiver 22, for example a CCD camera, fitted in the Scheimpflug arrangement. The light receiver 22 is set up to acquire and store a cross-sectional image of the cross-sectional part illuminated by the light projector 21 in the Scheimpflug arrangement with respect to the light beam. The triangulation module 35 is set up to determine the relative position B of the cornea 42 on the measurement axis z on the basis of the stored cross-sectional image. In the example according to FIG. 11, the axial length $L_A$ of the eye 4 results from $L_A = C_G + \Delta L_1 - \Delta L_2$, $\Delta L_1$ corresponding to the deflection of the variable reference arm 14, $\Delta L_2$ corresponding to the relative position B, determined by the non-interferometric measurement system 2, of the cornea 42, in particular of the vertex of the cornea 42, and $C_G$ corresponding to a geometrical system constant of the ophthanological measurement apparatus 10, specifically the distance of the reference zero points of the measuring ranges M1 and M2 of the interferometric and the non-interferometric measurement systems 1, 2. This can also be seen in FIG. 2, where $\Delta L_1$ corresponds to the measured value of the reference zero point $L_R$ of the measuring range M1 of the interferometric measurement system 1 up to the relative position A of the retina 41; where $\Delta L_2$ corresponds to the measured value of the reference zero point of the measuring range M2 of the non-interferometric measurement system 2 up to the relative position B of the cornea 42; and where the geometrical system constant $C_G$ corresponds to the distance between the reference zero points of the measuring ranges M1 and M2.

In the design variant according to FIG. 10b, the light projector 21 is set up to move the light beam 5 or the (shaped) ray bundle in order to scan the eye 4 or move the cornea 42 such that the light receiver 22, for example a CCD camera, can detect light which is diffusely reflected and, if appropriate, scattered in the eye tissue and is projected onto the eye 4 in various projection directions, for example in various projection planes. The light receiver 22 is arranged to detect the light along the measurement axis z. The light projector 21 is arranged outside the measurement axis z. The optional triangulation module 35 is set up to determine the relative position B of the cornea 42, in particular of the vertex of the cornea 42, from the detected light reflections and, if appropriate, light scatterings, by means of triangulation methods.

Before the use of the ophthalmological measurement apparatus 10 for determining the axial eye length $L_A$, the anterior chamber depth $L_{VK}$, the corneal thickness and/or the thickness $D_L$ of the lens 43, it is preferred to perform a calibration, for example on the basis of a reference body or calibration body. Depending on the design variant, the calibration body is a reference object which is, for example, designed in the form of an artificial eye and is fitted on the ophthalmological measurement apparatus 10 and can be pivoted for calibration purposes into the measuring range M1, M2, M3, or which can be fitted on the ophthalmological measurement apparatus 10 not permanently, but in a removable fashion simply for the calibration. In one design variant, the calibration body is designed as an artificial eye which comprises two boundary surfaces of known spacing (for example optical path length). The artificial eye can have a curved cornea, for example. In order to increase the detectability, the calibration body can also be of flat design so as to avoid interference rings. The cornea (that is to say front boundary surface) can also have a defined thickness in order to enable measurement with the aid of triangulation methods. In a further design variant, the calibration is performed via a boundary surface which can be measured by the two measurement systems 1, 2. That is to say, the measuring ranges M1 and M2 overlap one another, or one measuring range can temporarily be displaced into the other with a known path. For example, the measuring range M2 of the interferometric measurement system 1 can be displaced via a moveable reference mirror. If it is also possible to detect a curved cornea, the human eye can then also be used as reference body. Finally, the calibration can also be executed via a boundary surface which can be displaced from one measuring range into the other in a fashion defined via a movement driver.

A first relative position of the reference body is determined by means of the non-interferometric measurement system 2. In addition, a second relative position of the reference body is determined by means of the optical interferometric measurement system 1. Thereafter, a deviation between the first relative position of the reference body and the second relative position of the reference body is determined, stored and taken into account when determining the eye dimensions, particularly for determining the axial length $L_A$ of the eye 4. Depending on the design variant of the ophthalmological measurement apparatus 10, the following variants result for the measurement process for contactlessly determining the axial eye length $L_A$:

a) Uninterruptedly and continuously determining the relative position A of the retina 41 by means of the optical interferometric measurement system 1, and the relative position B of the cornea 42 by means of the non-interferometric measurement system 2, and continuously calculating the axial eye length $L_A$ on the basis of the current values of the relative position A of the retina 41 and of the relative position B of the cornea 42. The value of the axial eye length $L_A$ is, for example, not indicated until the value is adjusted within a defined fluctuation range.

b) Positioning the ophthalmological measurement apparatus 10 for detecting the measuring range M2 by means of the non-interferometric measurement system 2, and determining and storing the relative position B of the cornea 42 by means of the non-interferometric measurement system 2. Automatically activating the interferometric measurement system 1 in order to determine and store the relative position A of the retina 41 when the relative position B of the cornea 42 is detected by the non-interferometric measurement system 2. Calculating the axial eye length $L_A$ on the basis of the (temporarily) stored values of the relative position A of the retina 41 and of the relative position B of the cornea 42.

c) Positioning the ophthalmological measurement apparatus 10 for detecting the measuring range M1 by the interferometric measurement system 1, and determining and storing the relative position A of the retina 41 by means of the interferometric measurement system 1. Automatically activating the non-interferometric measurement system 2 for determining and storing the relative position B of the cornea 42 when the relative position A of the retina 41 is detected by the interferometric measurement system 1. Calculating the axial eye length $L_A$ on the basis of the stored values of the relative position A of the retina 41 and of the relative position B of the cornea 42.

It may further be remarked that, depending on the design of the non-interferometric system, the latter can be used to measure the corneal thickness, the anterior chamber depth and the lens thickness.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An ophthalmological measurement apparatus for determining the axial length of an eye, comprising:
   an optical interferometric first measurement system for determining a relative position of the retina of the eye,
   a non-interferometric second measurement system for determining a relative position of the cornea of the eye, the second measurement system including a distance measurement system for determining the relative position of the cornea on the basis of light diffusely reflected and/or scattered by the eye, and
   processing means for determining the axial length of the eye on the basis of the relative position of the retina and of the relative position of the cornea.

2. The measurement apparatus according to claim 1, wherein the second measurement system comprises a distance measurement system for determining the relative position of the cornea on the basis of light specularly reflected by the cornea.

3. The measurement apparatus according to claim 1, wherein the second measurement system comprises a light projector for projecting at least one light beam onto the cornea, the second measurement system comprises a light receiver connected to the processing means, and the processing means are configured to determine the relative position of the cornea on the basis of a signal received by the light receiver.

4. The measurement apparatus according to claim 3, wherein the light projector is configured to project two light beams intersecting at a crossing point, and the light receiver is configured to detect a positioning of the crossing point on the cornea in order to determine the relative position of the cornea.

5. The measurement apparatus according to claim 3, wherein the second measurement system comprises an optical system for focussed projection of the light beam onto the cornea, the second measurement system comprises a pinhole diaphragm placed upstream of the light receiver, the optical system and the pinhole diaphragm being arranged such that the light beam reflected by the cornea is fed to the light receiver via the optical system and through the pinhole diaphragm in order to determine the relative position of the cornea.

6. The measurement apparatus according to claim 2, wherein the distance measurement system comprises an autofocus sensor for determining the relative position of the cornea.

7. The measurement apparatus according to claim 3, wherein the distance measurement system comprises a sensor for detecting wavelength-dependent focal points when focussing a broadband light source with the aid of an optical system having strong chromatic aberrations, and the processing means are configured to determine the relative position of the cornea on the basis of the chromatic aberrations.

8. The measurement apparatus according to claim 1, wherein the light projector is configured to project the light beam along a measurement axis through a cross-sectional part of the cornea, the light receiver is configured to acquire and store a cross-sectional image of the cross-sectional part, illuminated by the light projector, in the Scheimpflug arrangement with respect to the light beam, the first measurement system is configured to determine the relative position of the retina on the measurement axis, and the processing means are configured to determine the relative position of the cornea on the measurement axis on the basis of the cross-sectional image.

9. The measurement apparatus according to claim 1, wherein the first measurement system comprises an apparatus for optical coherence tomography with depth scanning.

10. The measurement apparatus according to claim 1, wherein the first measurement system and the second measurement system are connected to the processing means and are configured to transmit continuously to the processing means signals for determining the current relative position of the retina and for determining the current relative position of the cornea, and the processing means are configured to determine a currently ascertained value of the axial length of the eye on the basis of the current relative position of the retina and the current relative position of the cornea.

11. The measurement apparatus according to claim 1, wherein the first measurement system is coupled to the second measurement system such that a signal from the first measurement system indicating the detection of the relative position of the retina automatically activates the second measurement system to determine the relative position of the cornea.

12. The measurement apparatus according to claim 11, wherein the first measurement system comprises an apparatus for optical coherence tomography with a reference arm length which can be varied in order to determine the relative position of the retina, and the first measurement system is coupled to the second measurement system such that, at the current position of the reference arm length, the signal indicating the detection of the relative position of the retina automatically activates the second measurement system in order to determine the relative position of the cornea.

13. The measurement apparatus according to claim 1, wherein the second measurement system comprises a light barrier system for detecting a vertex of the cornea as relative position of the cornea, and the light barrier system is coupled to the first measurement system such that the detection of the vertex automatically activates the first measurement system in order to determine the relative position of the retina.

14. The measurement apparatus according to claim 1, wherein the first measurement system is further configured to determine a relative position of a front side, facing the cornea, of the lens of the eye, and the processing means are additionally configured to determine the anterior chamber depth of the eye on the basis of the relative position of the cornea and of the relative position of the facing front side.

15. The measurement apparatus according to claim 1, wherein the first measurement system is further configured to determine a relative position of a rear side, averted from the cornea, of the lens, and the processing means are further configured to determine a thickness of the lens on the basis of a relative position of a front side, facing the cornea, of the lens of the eye and of the relative position of the averted rear side.

16. The measurement apparatus according to claim 1, wherein the first measurement system and the second measurement system each comprise a light source for generating a light beam, the wavelengths of the light beams generated by the light sources being different from one another.

17. The measurement apparatus according to claim 1, wherein the first measurement system and the second measurement system are configured such that the determination of the relative position of the retina and the determination of the relative position of the cornea are performed substantially simultaneously in order to determine the axial length of the eye.

18. The measurement method for contactlessly determining the axial length of an eye, comprising:
   determining a relative position of the retina of the eye by means of an optical interferometric measurement system,
   determining a relative position of the cornea of the eye by means of a non-interferometric measurement system on the basis of light diffusely reflected and/or scattered by the eye using a distance measurement system included in a second measurement system, and
   determining the axial length of the eye using processing means configured for determining the axial length of the eye based on the relative position of the retina and the relative position of the cornea.

19. The measurement method according to claim 18, wherein a vertex of the cornea is detected as relative position of the cornea by means of a light barrier system, and upon the detection of the vertex the optical interferometric measurement system is automatically activated in order to determine the relative position of the retina.

20. The measurement method according to claim 18, wherein the relative position of the retina is determined by means of an apparatus for optical coherence tomography, a reference arm length being varied in order to determine the relative position of the retina, and when a signal indicating the relative position of the retina is obtained the relative position of the cornea is automatically determined at the current position of the reference arm length by means of the non-interferometric measurement system.

21. The measurement method according to claim 18, wherein before the determination of the relative position of the retina and of the relative position of the cornea, a first relative position of a reference body is determined by means of the non-interferometric measurement system, a second relative position of the reference body is determined by means of the optical interferometric measurement system, and deviations between the first relative position of the reference body and the second relative position of the reference body are acquired and taken into account when determining the axial length of the eye.

22. The measurement apparatus according to claim 3, wherein the light projector is configured to project the light beam along a measurement axis through a cross-sectional part of the cornea, the light receiver is configured to acquire and store a cross-sectional image of the cross-sectional part, illuminated by the light projector, in the Scheimpflug arrangement with respect to the light beam, the first measurement system is configured to determine the relative position of the retina on the measurement axis, and the processing means are configured to determine the relative position of the cornea on the measurement axis on the basis of the cross-sectional image.

23. The measurement apparatus according to claim 1, wherein the processing means comprises a processor.

24. The measurement method according to claim 18, wherein the processing means comprises a processor.

* * * * *